United States Patent [19]
Levy et al.

[11] Patent Number: 6,113,589
[45] Date of Patent: Sep. 5, 2000

[54] FIBER AND A DEVICE INCORPORATING THE FIBER THEREIN FOR USE IN TREATING TISSUE VOLUMES

[75] Inventors: Uri Levy, Rehovot; Orit Frankel, Hod Hasharon; Ytzhak Rosenberg, Ramat Gan; Raphi Seror, Petach Tikva, all of Israel

[73] Assignee: Laser Industries Ltd., Israel

[21] Appl. No.: 09/050,788

[22] Filed: Mar. 30, 1998

Related U.S. Application Data

[63] Continuation-in-part of application No. 08/576,487, Dec. 21, 1995, Pat. No. 5,773,279.

[51] Int. Cl.⁷ .................................................. A61B 17/36
[52] U.S. Cl. ........................................................ 606/16
[58] Field of Search ............................ 606/16, 17; 607/88

[56] References Cited

U.S. PATENT DOCUMENTS

| | | |
|---|---|---|
| 5,401,270 | 3/1995 | Muller et al. ......................... 606/17 |
| 5,449,354 | 9/1995 | Konwitz . |
| 5,733,279 | 3/1998 | Konwitz . |

*Primary Examiner*—William E. Kamm
*Attorney, Agent, or Firm*—Eitan, Pearl, Latzer & Cohen-Zedek

[57] ABSTRACT

A device for use in laser induced interstitial thermotherapy (LITT) is provided which includes a fiber for coupling to a laser energy source and an emitting element having a proximal end coupled to the fiber and a distal end for positioning adjacent to the surface receiving LITT, the emitting element radially emitting light whose intensity is controllable along its longitudinal length. In a preferred embodiment, the surface of the emitting element is roughened to achieve a power scattering function.

20 Claims, 6 Drawing Sheets

FIBER AND A DEVICE INCORPORATING THE FIBER THEREIN FOR USE IN TREATING TISSUE VOLUMES

RELATED APPLICATIONS

This application is a continuation in part application of patent application Ser. No. 08/576,487 filed Dec. 21, 1995, to be issued as U.S. Pat. No. 5,733,279.

FIELD OF THE INVENTION

The present invention relates to a device for use in laser induced interstitial thermotherapy (LITT).

BACKGROUND OF THE INVENTION

Destruction of volumes of tissue in the human body is desired in many situations. Such is the case with the most common problem of expanded male prostate, and the case of benign and malignant tumors in the liver, breast or brain. And such is the case of the uterine layer (endometrium) of excessively bleeding women.

Excessive and/or prolonged menstrual bleeding (or chronic menorrhagia), is commonly treated by birth control pills, other hormonal therapies, or by a minor operation called "D and C" (dilation and curettage) involving a scraping of the lining of the uterus. When such treatments are not effective, a hysterectomy is generally performed which involves removing the uterus and the lining along with it. Approximately 600,000 hysterectomies are performed in the USA each year.

One method of tissue destruction is known as interstitial thermo-therapy (ITT). In this method, the tissue temperature is elevated (above a certain threshold temperature for a certain duration) by absorption of (laser) light. Light, in turn, is transmitted to the scene via an optical fiber and is scattered and diffused to be absorbed by the volume of tissue to be destroyed. Usually, the light source is a laser, such as a Nd:YAG laser system or Diode laser system.

Recently, a technique has been developed using laser energy to ablate the uterine lining such as to cause scarring that prevents the lining from growing back. In this technique, a laser beam is conducted in the uterus by means of an optical fiber. The optical fiber is inserted via a channel of a hysteroscope, enabling the physician to view the interior of the uterus as the physician manipulates the tip of the optical fiber. The physician sweeps the tip of the optical fiber across the uterine lining to ablate the lining to a depth of about 3–5 mm. This procedure is carried out under general anesthesia by a skilled operator, is time consuming and there is a risk of uterine perforation.

An alternative technique is to slowly elevate the temperature of the whole surface being treat simultaneously. This is carried out by scattering light from the optical fibers. The fibers used for transmitting and diffusing the laser light are generally known as induced interstitial thermotherapy (ITT) fibers.

ITT fibers are well known. An example of an optical device which uses ITT fibers is described in U.S. Pat. No. 5,449,354 which discloses a device for treating the interior of a body cavity with laser energy particularly useful for the procedure. The described apparatus comprises at least two optical fibers each having a distal end adapted to be inserted into the body cavity to be treated, and a proximal end to be located externally of the body cavity and to be coupled to a source of laser energy. One of the optical fibers is axially movable with respect to the other optical fiber to either a retracted, non-operative position or to an extended, operative position. The distal ends of the two optical fibers are mechanically coupled together such that movement of one optical fiber axially with respect to the other causes the distal ends of the two optical fibers to spread apart laterally, and to direct the laser energy outwardly of the optical fibers.

In the preferred embodiment described in that patent, the optical fibers are disposed within a cannula having a distal end adapted to be inserted into the body cavity to be treated, and a proximal end to be located externally of the body cavity when the distal end is inserted therein. In the described device, there were three optical fibers within the cannula arranged in side-by-side relation, with two of the fibers being outer fibers, and the third fiber being the middle fiber straddled on opposite sides by the two outer fibers. The two outer fibers are axially movable with respect to the middle fiber; and the distal ends of the three fibers are mechanically coupled together such that movement of the two outer fibers axially with respect to the middle fiber causes the distal ends of all three fibers to spread apart laterally.

As described in U.S. Pat. No. 5,449,354, such a laser device is particularly useful for treating chronic menorrhagia since a single dosage of laser energy will substantially cover most or all of the uterine lining. Thus, the device avoids the need for the physician to view the interior of the uterus, and thereby the need for inserting a hysteroscope into the uterus. In addition, it reduces, or perhaps may even eliminate, the dilation required of the uterus, and also substantially reduces the time of treatment. Local anesthesia can be used and the procedure can be carried out with minimal training at lower risk to the patient.

U.S. Pat. No. 5,733,279 discloses a further device for treating the interior of a body cavity with laser energy without the need for a cannula, thereby reducing the dilation required of the uterus during treatment. The apparatus describes a device having at least two outer fibers and a middle fiber, in side-by-side relation each having a distal end to be inserted into the body cavity to be treated, and a proximal end to be located externally of the body cavity and to be coupled to a source of laser energy; and actuator means coupled to the optical fibers. In the preferred embodiment described in that patent, the actuator means comprises rods for coupling each of the outer fibers to the middle fiber, one end of the rods is pivotally connected to each of the distal ends of the outer fibers and the other end is pivotally connected to the middle fiber. This arrangement allows for manually activating the proximal end of the outer fibers to move axially with respect to the middle fiber so that the distal ends of the fibers spread.

Some of the prior art designs are not heat-durable and it is very difficult to control the intensity of the light being diffused.

SUMMARY OF THE INVENTION

An object of the present invention is to provide a device for use in laser induced interstitial thermotherapy (LITT) which allows for controlling the intensity of the radially emitting light along the longitudinal length of the fiber.

A further object of the present invention is to provide a device which uses a light emitting element coupled to the optical fibers for scattering (or diffusing) the light. The light emitting element is configured for controlled scattering by roughening the surface or by adding grooves to the surface.

It is a yet further object of the present invention to provide a device which incorporates a detachable cover that allows the main optical fibers to be reused several times.

There is thus provided, in accordance with a preferred embodiment of the present invention, a device for use in laser induced interstitial thermotherapy (LITT) which includes a fiber for coupling to a laser energy source and an emitting element having a proximal end coupled to the fiber and a distal end for positioning adjacent to the surface receiving LITT, the emitting element radially emitting light whose intensity is controllable along its longitudinal length.

In a preferred embodiment, the surface of the emitting element is roughened to achieve a power scattering function. The light intensity increases monotonically along the length of the emitting element Furthermore, in accordance with a preferred embodiment of the present invention, the surface of the emitting element includes a plurality of grooves and the intensity of the emitted light is controlled by the depth and density of the plurality of grooves.

Furthermore, in accordance with a preferred embodiment of the present invention, the fiber is reusable and further includes a detachable cover for protecting the emitting element, the detachable cover being disconnectably attached to the fiber. The distal end of the detachable cover is transparent to the radiation being emitted.

Furthermore, in accordance with a preferred embodiment of the present invention, the emitting element may be a diffusing rod attached to the optical fiber or the optical fiber itself.

In addition, there is provided, in accordance with a preferred embodiment of the present invention, an optical fiber for use in laser induced interstitial thermotherapy (LITT) which has a proximal end for coupling to a laser energy source and a distal end for positioning adjacent to the tissue volume receiving LITT. The surface of the distal end is roughened so as to control the intensity of the radially emitting light along the fiber's longitudinal length.

Additionally, there is provided, in accordance with a preferred embodiment of the present invention, a device for use in laser induced interstitial thermotherapy (LITT) which includes at least two fibers in side-by-side relation each having a proximal end for coupling to a laser energy source and a plurality of emitting elements, each of which has a proximal end for coupling to each of the at least two fibers and a distal end for positioning adjacent to the surface receiving LITT. Each of the plurality of the emitting element radially emit light whose intensity is controllable along its longitudinal length.

In another preferred embodiment, the device includes two outer fibers and a third inner fiber in side-by-side relation each having a proximal end for coupling to a laser energy source.

Furthermore, in accordance with a preferred embodiment of the present invention, the device further includes an operating handpiece having a plurality of covers integrally formed therewith for enclosing the ends of the fibers proximate to the proximal end of each of the plurality of emitting elements. The operating handpiece includes activating means for individually activating the distal end of each of the plurality of emitting elements to move axially thereby to change their relative position with respect to each other.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figures 1A, 1B:
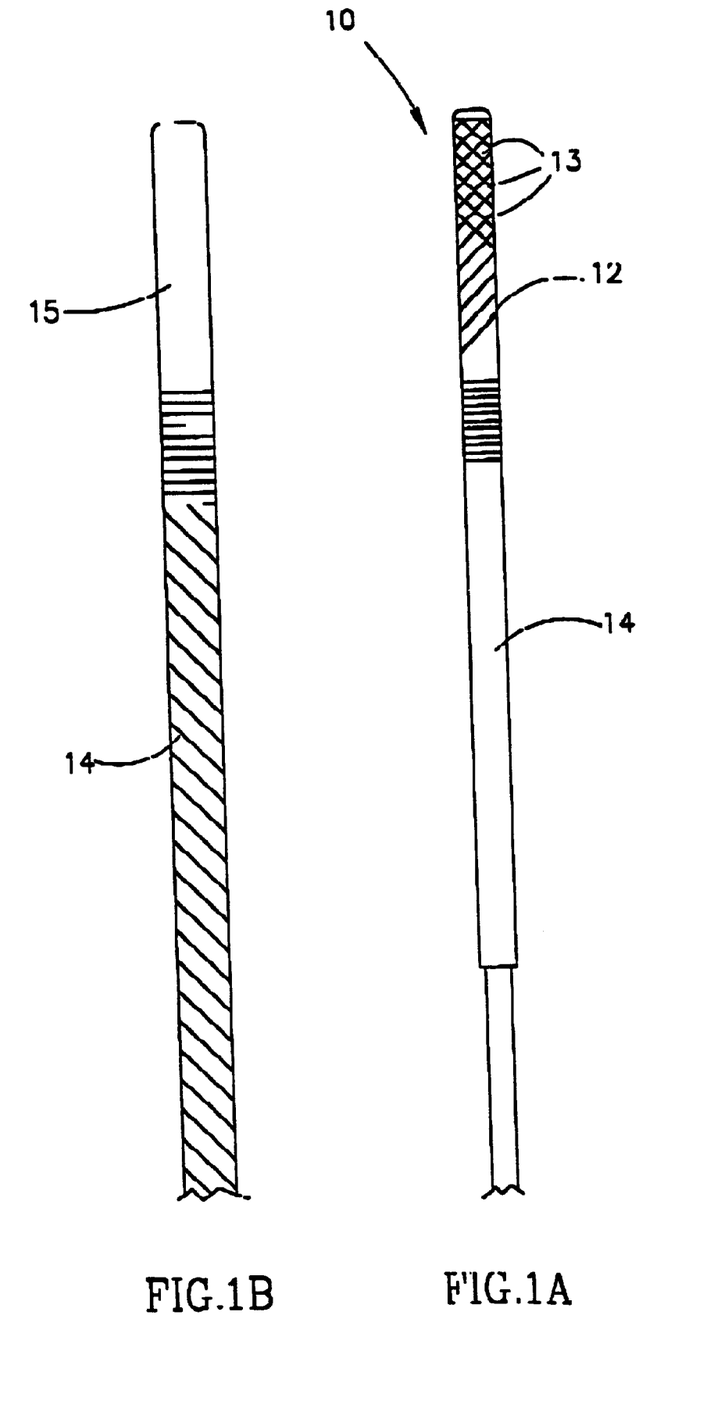
FIGS. 1A and 1B are sectional views of an induced interstitial thermotherapy (ITT) fiber constructed in accordance with a preferred embodiment of the present invention.

Reference is now made to FIGS. 1A and 1B, which are sectional views of an induced interstitial thermotherapy (ITT) fiber generally designated 10, constructed in accordance with a preferred embodiment of the present invention. The ITT fiber 10 comprises a light scattering element 12 attached to an optical fiber 14, as shown in FIG. 1A. In order to control the intensity of light being emitted from the ITT fiber 10, the outer surface of the light scattering element 12 is modified (indicated by lines 13) so that the amount of light being emitted from the light scattering element 12 can be controlled. By suitably modifying the outer surface, the ITT fiber can be configured for the treatment of specific tissue volumes.

The light scattering element 12 may be a diffusing rod which is attached to the optical fiber 14 by fusing or any suitable means. Alternatively, the distal end of the ITT fiber 10 itself can be modified so as to act as the light scattering element for controlling the intensity of light.

The control of light intensity in both the longitudinal and azimuth axes of the light scattering element 12 can be achieved by controlled roughening of the outer surface or by indenting the outer surface with a plurality of grooves, for example.

FIG. 1B illustrates the ITT fiber 10 enclosed within a disposable cover 15, which is a longitudinal sleeve which is preferably translucent to the radiation being emitted from the fiber 10.

In an alternative embodiment, cover 15 may be non-translucent to the radiation, in which case treatment is effected by the heat, generated by the optical fiber 14, from the cover tip coming into contact with the tissue.

The disposable cover 15 is sufficiently long so that only the cover comes into contact with the part to be treated and the non-covered part of the optical fiber is kept outside the treatment area. Thus, the optical fibers 14, which do not come into contact with the treated tissue are protected against contamination and damage, can be reused. That is, after the treatment has been completed, the cover 15 is removed and disposed of. A new, sterile cover 15 is placed over the optical fibers 14 ready for the next treatment.

Figure 2:
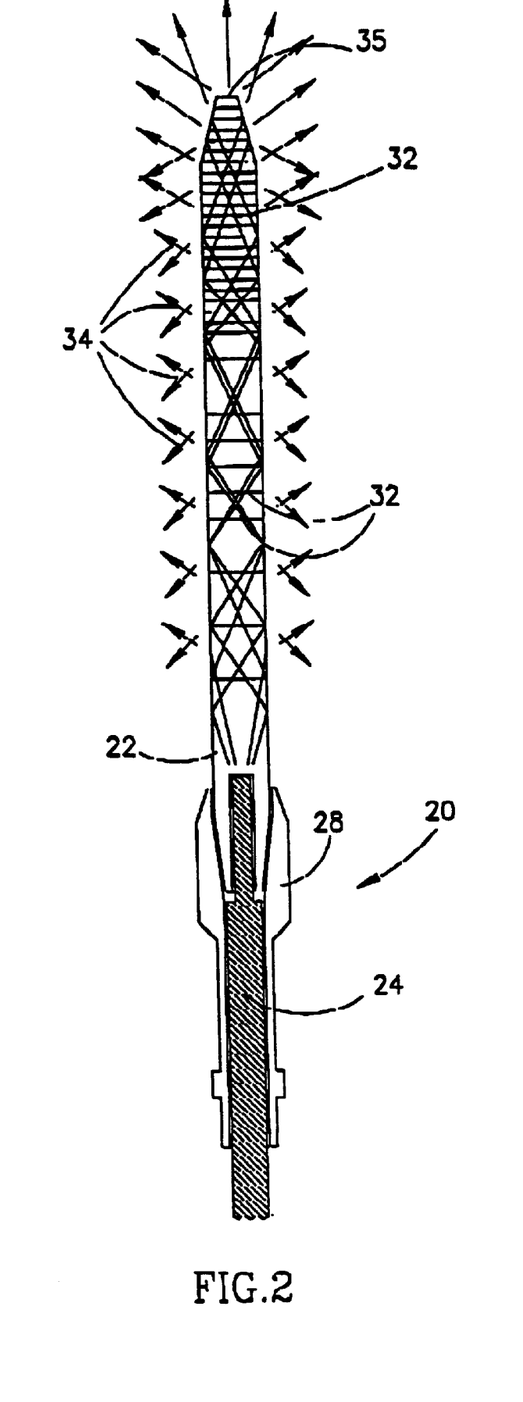
FIG. 2 is a sectional view of an ITT fiber constructed in accordance with a further preferred embodiment of the present invention.
Figure 3:
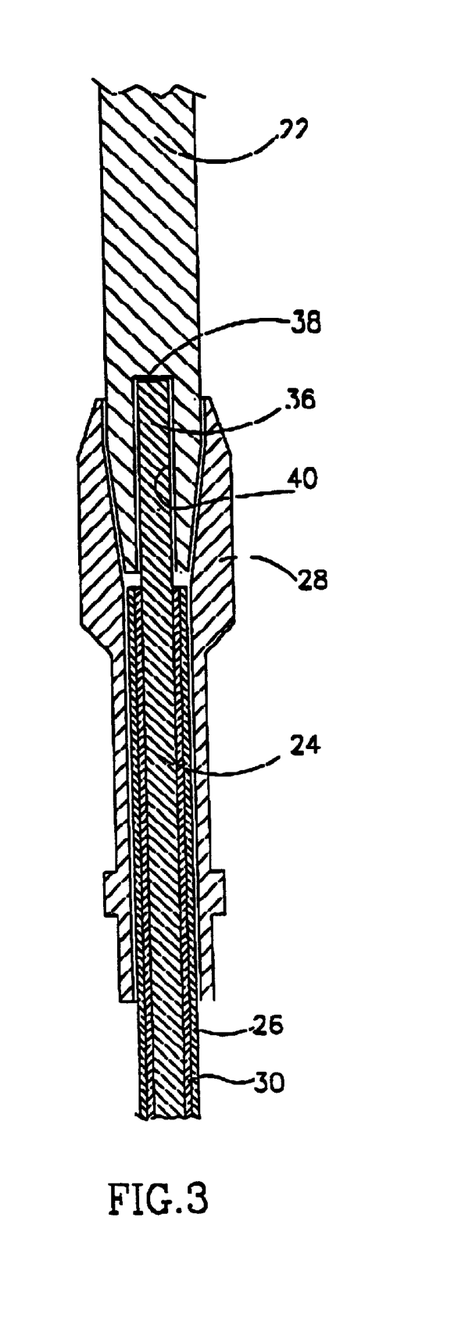
FIG. 3 is an enlarged sectional view of the ITT fiber of FIG. 2.

Reference is now made to FIGS. 2 and 3 which are sectional views of an ITT fiber, generally designated 20 constructed in accordance with a further preferred embodiment of the present invention.

The ITT fiber 20 comprises a diffusing rod 22 (which acts as the light scattering element) attached to an optical fiber 24.

ITT fiber 20 further comprises a crimping attachment 28 attached to and extending from an outer sleeve 26 of the optical fiber 24. The crimping attachment 28, which is firmly attached to an outer jacket 30 of optical fiber 24, retains the diffusing rod 22 thereby giving mechanical strength to the ITT fiber 20.

The diffusing rod 22 has a roughened surface formed from grooves, schematically indicated by groove lines 32, indented on the surface of diffusing rod 22. As the laser light from the optical fiber 24 propagates through the diffusing rod 22, it hits the groove lines 32 of the roughened surface and is partly scattered out of the diffusing rod, schematically represented by arrows 34.

The longitudinal and azimuth properties of the roughened surface strongly influence the longitudinal and azimuthal intensity of the scattered light. Various grooves with different shape, depth, orientation and density are relatively easily imposed on the surface to affect the scattered light intensity distribution. In the example of FIG. 2, the density of the grooves is increased (schematically illustrated by placing the lines 32 closer together) to scatter more light towards the distal end 35 of diffusing rod 22.

Azimuth scattering control can be achieved by either imparting cylindrical asymmetric grooves or by roughening the surface, as described hereinabove, or optionally, by depositing a layer of mirrored metal on the outer surface of the diffusing rod 22.

As best seen in FIG. 3, optical fiber 24 comprises a protruding tip 36 which is continuation of the core 38 of the optical fiber 24 and diffusing rod 22 comprises a channel 40 to receive the protruding tip 36. The interface 38 between the protruding tip 36 and the diffusing rod 22 is formed such that little or no reflection or scattering takes place. This can be done by fusing the fiber tip to the diffusing rod or by introducing an index matching, high temperature adhesive, for example. As shown, crimping attachment 28, firmly attached to the outer sleeve 26 of the optical fiber 24, holds the diffusing rod 22 and prevents mechanical stress/strain forces on the relatively weak portion of the protruding tip 36.

Figure 4:
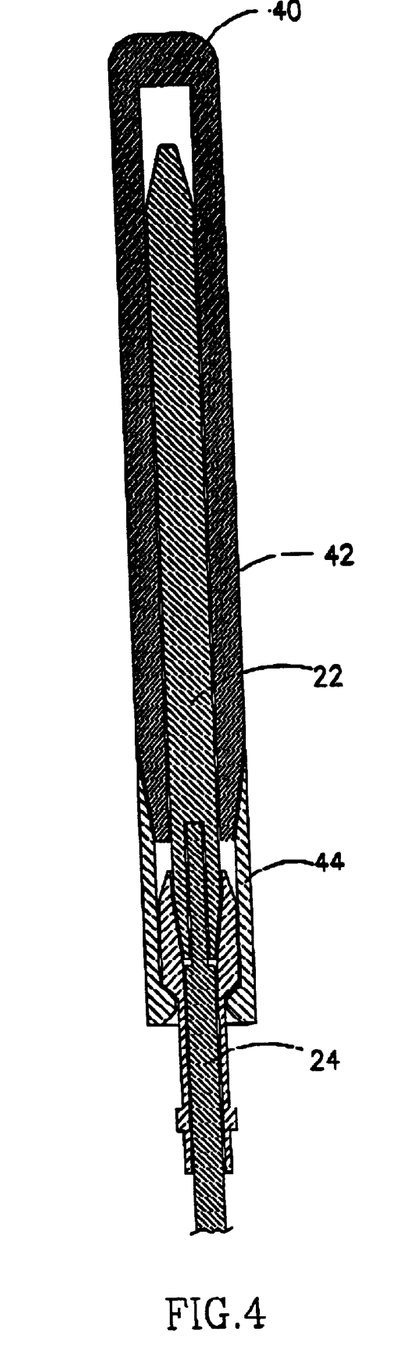
FIG. 4 is a sectional view of the connect/disconnect cover.
Figure 5:
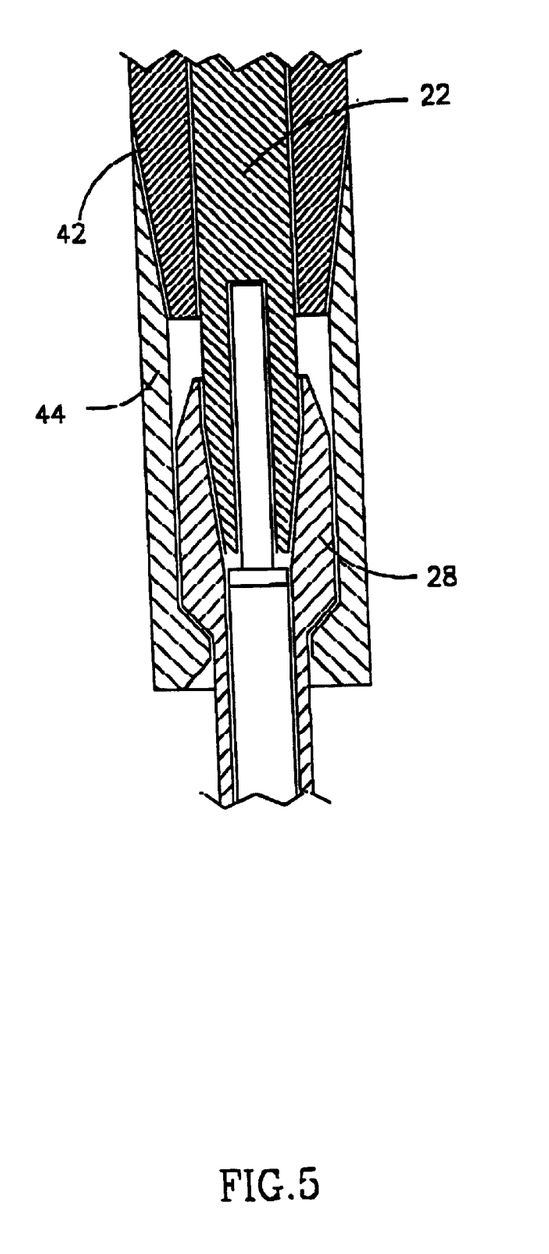
FIG. 5 is an enlarged sectional view illustration of the ITT fiber within the connect/disconnect cover of FIG. 4.

The crimping attachment 28 may also used as an anchor for the connect/disconnect cover 40, which is illustrated in FIGS. 4 and 5, to which reference is now made. The cover in its "connected" position is shown in FIGS. 4 and 5.

Cover 40 comprises a transparent cover tube 42 attached to a snap element 44. The cover tube 42 manufactured from glass or a transparent plastic, for example, is connected to the snap element 44, which is preferably made of metal or plastic. Snap element 44 is designed to quickly connect to crimping attachment 28 by pushing the cover 40 against the protruding tip 36. Upon being pushed together, the flexible 'flaps' of the snap element 44 expand and then return to their neutral position as the snap element 44 moves further with respect to the crimping attachment 28.

As the laser light from the optical fiber 24 propagates through the diffusing rod 22, it is scattered at the rough surface of diffusing rod 22 and propagated through the transparent cover tube 42 to be absorbed by the surrounding tissue (not shown).

The cover tube 42 and the snap element 44 surround the diffusing rod 22 and crimping attachment 28.

Since the protruding tip 36 is protected by the cover 40 against mechanical damage and contamination, it can be reused many times by simply disconnecting the used cover and connecting a new sterile cover.

Figure 6:
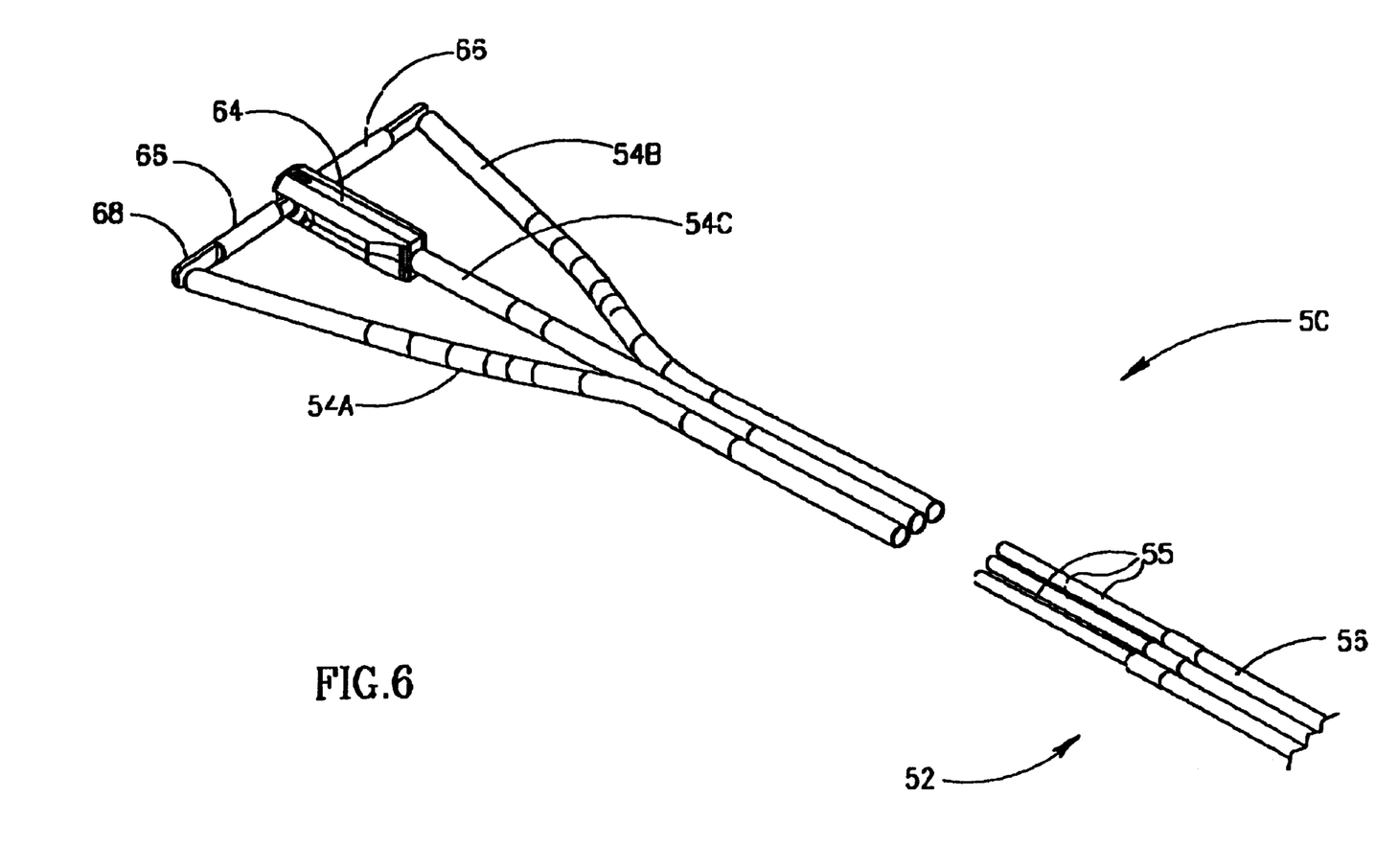
FIG. 6 is an isometric view of one form of a device utilizing a plurality of ITT fibers of FIG. 1, constructed in accordance with a preferred embodiment of the present invention.

Multiple fibers can be assembled for various applications, for example, in cases where it is desired to destroy a large volume of tissue. Reference is now made to FIG. 6, which is an isometric view of one form of an Endometrial Laser Interstitial Thermo-Therapy (ELITT) device, generally designated 50, utilizing a plurality of ITT fibers, generally designated 52, constructed in accordance with a preferred embodiment of the present invention. Device 50 allows for insertion of the three ITT fibers 52 enclosed within covers 54 through the cervix into the uterus, for example, spreading of the fibers inside the uterus, "folding" the fibers after the heating phase and pulling them out of the treated uterus.

Each of ITT fibers 52 are similar to ITT fiber 10 described hereinabove with respect to FIG. 1 and comprise either the fiber itself suitably modified or a light scattering element 55 attached to an optical fiber 56.

Preferably, each light scattering element 55 attached to an optical fiber 56 is protected by separate covers 54 similar to cover 40, described hereinabove. In an alternative embodiment, all three fibers may be enclosed within a single cover.

Figure 7:
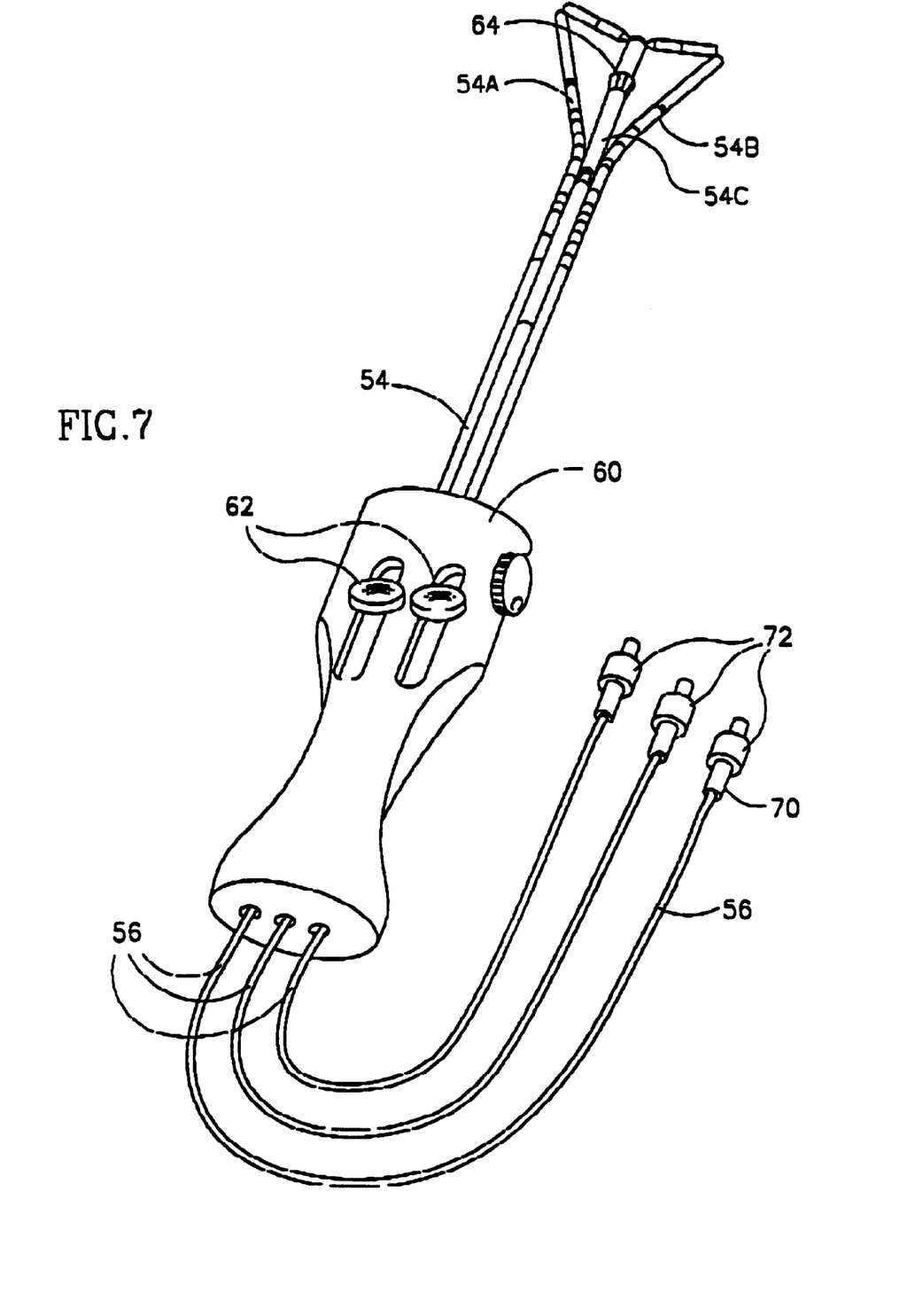
FIG. 7 is an isometric view of the device of FIG. 6, together with an operating handpiece, constructed in accordance with a preferred embodiment of the present invention.

Reference is now also made to FIG. 7 which illustrates an operating handpiece 60 for use with the three ITT fibers 52 (of FIG. 6). Operating handpiece 60 comprises two push/pull levers 62 attached to each of the outer ITT fibers 52 for individually moving each of the outer side scattering element covers, 54A and 54B, with respect to the center scattering element cover 54C. Thus, the device can be spread by pushing each of the outer side scattering element covers, 54A and 54B, separately (and hence the respective scattering element within the cover) to ease the operation and to ensure a better fit and to shape the spread-out device to the shape of the internal cavity of the uterus.

ELITT device 60 is similar to U.S. Pat. No. 5,449,354 to Konwitz and Donnez which describes the use of a three arm device of scattering fibers for endometrium destruction. Each arm is a scattering fiber, similar to ITT fiber 10 described hereinabove. The device is inserted through the cervix and into the uterus in its "folded" state and is then switched to its "spread" state by pushing the arms. After the heating cycle has been completed, the device is folded again and pulled out.

ELITT device 60 differs from the earlier U.S. Pat. No. 5,449,354 in the use of handpiece 62 described hereinabove and further by using a mechanical "director" 64 to improve the spread mechanism. In addition, since each of the light scattering element 55 are protected by a cover 54 which is disposable after use, the ITT fibers 52 may be reused by reinserting them within a new sterile and protecting cover 54, thereby reducing the cost of the medical treatment.

One method for assembling the light scattering element 55 can be described as follows, with particular reference to FIG. 6: Two outer side scattering element covers 54A and 54B are connected to a center scattering element cover 54C by means of a heat shrinkable flexible plastic tubing 66, or similar containing rigid spacers 68. The spacers 68 ensure a certain distance between each of the side scattering element covers (54A and 54B) and the center scattering element cover (54C) when the light scattering elements 55 are pushed forward. Mechanical director 64 is attached to the center scattering element cover 54C. Mechanical director 64 directs the side scattering element covers (54A and 54B) outwards, at the beginning of the forward movement of the side scattering element covers (54A and 54B).

ELITT device 60 is shown in its spread state (FIGS. 6 and 7). It should be noted that the spacers 68 need not be perpendicular to the center scattering element 55 within cover (54C). Each side scattering element (54A,54B) can be independently pushed until its spacer 68 and/or the tip of the side scattering element cover (54A, 54B) is butt against the uterine cavity (fundus).

In its folded position, the cross section circumference of the ELITT device 60 is small for easy insertion through the cervix.

FIG. 7 illustrates the complete three-fiber device having reusable optical fibers 56. Handpiece 60 is disposed close to the distal end. The operator holds the handpiece 60 when pushing the device into the uterine cavity and when pulling it out. The handpiece 60 includes a push/pull lever mechanism 62 for each of the side scattering elements 55 within covers (54A,54B) to spread/fold the tips of the scattering elements 55, as explained above. At the proximal end 70, the optical fibers 56 are terminated with standard fiber connectors 72. Each of these connectors 72, is connected to an intense light source, such as a laser system (not shown).

The light necessary for heating the tissue, generated at the light source (not shown), propagates through the connected fibers 56 to the distal end where it is scattered outwards (in a predetermined fashion, depending on the nature of the roughened surface, as described hereinabove) to be absorbed by the tissue, elevate its temperature and destroy it to the depth required.

It will be appreciated by persons skilled in the art that the present invention is not limited to the treatment of uterine tissue but the LITT device may be utilized to treat any tissue volume.

A description of surface roughness principles and a laser lathe realization method to achieve a given power scattering function will now be described with reference to Appendix A.

APPENDIX A

1. The Basic Idea
    a) For a given application, the (cylindrically symmetric) power per unit length scattering function (along a diffusing rod of length L) is known. For future reference we designate this known and desired function as $Phi_d(z)$. This function has the dimensions of watt/mm. The desired function $Phi_d(z)$ is known either by a guess or by theoretical calculations or by experimentation or by any other way.
    b) In our fiber/diffusing-rod design, it is possible to design and implement a certain surface roughness to achieve an actual scattering function $Phi_a(z)$ close to the given scattering function $Phi_d(z)$.

To be more specific, we can describe the surface roughness in terms of a Light Scattering Function [LSF(z)] with dimension of 1/mm such that $$-dP(z)/dz = Phi(z) = LSF(z) * P(z)$$

where $P(z)$ is the power inside the diffusing rod at distance z (from a given origin). $-dP(z)/dz$ is the fraction of power scattered out at the distance z.

2. Surface Roughness Principles

The relations between surface roughness and LSF become clear. Low LSF means "smooth" surface and high LSF means "rough" surface. The terms "smooth" and "rough" are explained below with reference to grooves and surface roughness.

2.1. Grooves

Assume that the roughness is achieved by ring grooves around the diffusing rod. Let us further assume that the grooves have a triangular cross-section at a given headangle. We can define two parameters—depth of the groove (h) and the distance between grooves (d). To change the surface "roughness" we can change either parameter or both. As h goes to 0 and d to infinity, the surface becomes very smooth. As h grows and d shrinks, surface roughness increases (and hence is the LSF). All this is a quantitative description. In practice—most likely—one needs several trial and error rounds to achieve a power scattering function close to the desired function $Phi_d(z)$.

Clearly the same principles apply to other groove shapes—non triangular cross-section and not arranged in rings. For example—trapezoidal cross-section and "diamond" arrangement.

2.2. Roughness

If the surface is rough—such as a glass surface after working on it with a sand-paper or after etching with some acid, it can also have "smooth" or "rough" nature, depending on the roughness parameters. Here the mathematics is more subtle but the principle is obvious. In practice, a coarse sand paper or a longer dip in chemicals will produce rougher surfaces.

3. Laser Grooves

A method of imparting grooves on the surface of the diffusing rod, known as "laser lathe" can be described, as follows:

3.1. Set-up

The diffusing rod is rotated about its axis of symmetry (z). A laser beam ($CO_2$) is focused onto its surface.

The position of the focused beam along the z axis can be varied by moving the diffusing rod up/down using—typically—a stepper motor. The speed of this z movement is computer controlled.

The exact plane of focus of the laser beam is controlled by moving a focusing lens with a second stepper motor. This focus movement is also computer controlled.

The output power from the laser can be selected in a certain range as needed.

Further beam can be blocked by a computer controlled "shutter".

3.2. Making the Grooves

The rod is rotated about its axis and the laser fires. At the same time the rod is translated along the z axis at a prescribed speed. The beam can be focused/defocused and turned on/off during the process. Helical groves are formed with varying density and depth as desired. A diamond shape is formed in a "double-pass" process with the rod rotated clockwise and than counterclockwise.

4. Examples 4.1. Increasing Power Scattering

Assume that we want to obtain a power scattering function that is low at the proximal end of the diffusing rod and high at the distal end (such function is desired for endometrial photocoagulation). We start laser grooving at the proximal end and move fast and possibly use a relatively low power beam and/or defocused beam. We gradually slow down and possibly increase the laser power and/or focus the beam as we move towards the distal end. This way we achieve a relatively smooth surface at the proximal end, growing gradually to a rough surface as we move towards the distal end. Such roughness function will yield the desired increasing power scattering function 4.2. Decreasing Power Scattering This case is much easier than the previous case as more or less uniform surface roughness will yield a decreasing power scattering function (moving from proximal end to distal end). By small adjustments of the groove parameters, we can control the decrease rate as desired. Clearly, essentially uniform power scattering is achievable.

4.3. Other Scattering Shapes

Obviously—within certain limits, non monotonic power scattering functions can be achieved.

4.4. Example of a Measured Light Distribution Function

Figure 8:
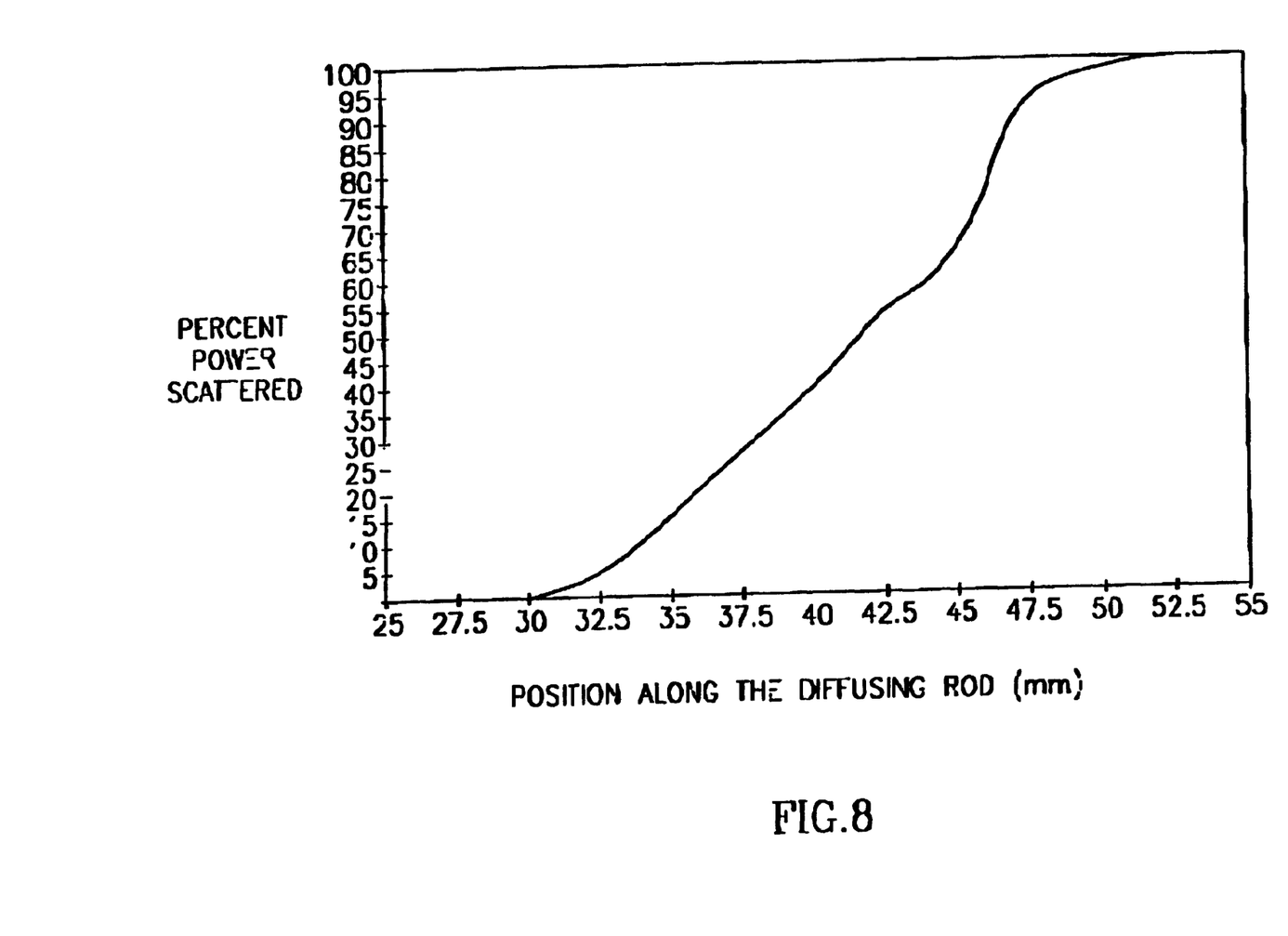
FIG. 8 is a graph illustrating the total power of the diffusing rod as a function of its longitudinal length.

FIG. 8 shows the total power from a part of the diffusing rod as a function of the length of that part. Looking at the curve, we can see that indeed the proximal end of the diffusing rod scatters a small fraction of the power while most of the power is scattered from the distal end.

5. Summary

By controlling the roughing process we can control the surface roughness parameters that in turn determine the power scattering function.

While the invention has been described with respect to one preferred embodiment, it will be appreciated that this is set forth merely for purposes of example, and that many other variations, modifications and applications of the invention may be made.

What is claimed is:

1. A device for use in laser induced interstitial thermotherapy (LITT) comprising:
    at least two fibers in side-by-side relation each having a proximal end for coupling to a laser energy source;
    a plurality of emitting elements, each of which has a proximal end for coupling to each of said at least two fibers and a distal end for positioning adjacent to the surface receiving; and
    an operating handpiece having a plurality of covers integrally formed therewith for enclosing the ends of said at least two fibers proximate to the proximal end of each of said plurality of emitting elements,
    wherein each of said plurality of said emitting elements radially emit light whose intensity is controllable along its longitudinal length.

2. A device according to claim 1 wherein the surface of each of said emitting elements is roughened and the intensity of said emitted light is controlled by the amount of surface roughness of each of said emitting elements.

3. A device according to claim 1 wherein the surface of each of said emitting elements comprises a plurality of grooves and wherein the intensity of said emitted light is controlled by the depth and density of said plurality of grooves.

4. A device according to claim 1 wherein each of said plurality of fibers is reusable and further comprising a plurality of detachable covers for protecting each of said emitting elements, each of said plurality of detachable covers protecting a corresponding one of said plurality of said emitting elements, each of said plurality of detachable covers being disconnectably attached to each of said fibers.

5. A device according to claim 1 wherein the light intensity increases monotonically along the length of each of said emitting elements.

6. A device according to claim 1 wherein each of said emitting elements is a diffusing rod.

7. A device according to claim 1 wherein each of said emitting elements is an optical fiber.

8. A device according to claim 4 wherein the distal end of the detachable cover of each of said emitting elements is transparent to the radiation being emitted.

9. A device according to claim 1 and further comprising a detachable cover for protecting said plurality of emitting elements, said detachable cover being disconnectably attached to said plurality of fibers.

10. A device according to claim 1 and further comprising connecting rods for pivotally coupling the ends of each of said plurality of emitting elements proximate to their said distal ends.

11. A device according to claim 1 wherein said operating handpiece comprises activating means for individually activating the distal end of each of said plurality of emitting elements to move axially thereby to change their relative position with respect to each other.

12. A device according to claim 1 further comprising a third fiber in side-by-side relation to said two fibers and wherein said third fiber has a proximal end for coupling to said laser energy source.

13. A device for use in laser induced interstitial thermotherapy (LITT) comprising:
    two outer fibers and a third inner fiber in side-by-side relation each having a proximal end for coupling to a laser energy source;
    a plurality of emitting elements, each of which has a proximal end for coupling to each of said two outer fibers and said third inner fiber and a distal end for positioning adjacent to the surface receiving LITT;
    wherein each of said plurality of said emitting element radially emit light whose intensity is controllable along its longitudinal length; and
    an operating handpiece having a plurality of covers integrally formed therewith for enclosing the ends of said two outer fibers and said third inner fiber proximate to the proximal end of each of said plurality of emitting elements.

14. A device according to claim 13 wherein said operating handpiece comprises activating means for individually activating the distal end of each of said plurality of emitting elements attached to said two outer fibers to move axially thereby to change their relative position with respect to the emitting elements attached said third inner fiber.

15. A fiber for use in laser induced interstitial thermotherapy (LITT) comprising an optical fiber having a proximal end for coupling to a laser energy source and a distal end for positioning adjacent to the tissue volume receiving LITT, wherein the surface of said distal end is roughened thereby to control the intensity of the radially emitting light along the fiber's longitudinal length.

16. A device according to claim 15 wherein said fiber is reusable and further comprising a detachable cover for protecting said distal end, said detachable cover being disconnectably attached to said fiber.

17. A device according to claim 16 wherein the distal end of said detachable cover is transparent to the radiation being emitted.

18. A device according to claim 15 wherein the surface of said distal end comprises a plurality of grooves and wherein the intensity of said emitted light is controlled by the depth and density of said plurality of grooves.

19. A disposable handpiece for use in laser induced interstitial thermotherapy (LITT) comprising at least two covers integrally formed therewith for enclosing and protecting the respective ends of at least two optical fibers, wherein each of said at least two optical fibers are reusable.

20. A device according to claim 19 wherein said disposable handpiece comprises activating means for individually activating the distal end of each of said at least two optical fibers to move axially thereby to change their relative position with respect to each other.

* * * * *